United States Patent [19]

Bailey

[11] 4,182,895

[45] Jan. 8, 1980

[54] 1-AMINO-LOWER-ALKYL-3,4-DIPHENYL-1H-PYRAZOLES

[75] Inventor: Denis M. Bailey, East Greenbush, N.Y.

[73] Assignee: Sterling Drug Inc., New York, N.Y.

[21] Appl. No.: 924,677

[22] Filed: Jul. 14, 1978

Related U.S. Application Data

[62] Division of Ser. No. 752,316, Dec. 20, 1976, abandoned.

[51] Int. Cl.$^2$ ............................................. C07D 231/12
[52] U.S. Cl. ................................. 548/378; 424/273 P
[58] Field of Search ........................................ 548/378

[56] References Cited

PUBLICATIONS

Grandberg et al., Zh. Obshch. Khim., 1961, vol. 31, pp. 3700–3705.
Torf et al., Chem. Abst., 1965, vol. 63, #16329e.
Noguchi et al., Chem. Abst., 1971, vol. 74, #22836g.
Jones et al., J. Org. Chem., 1954, vol. 19, pp. 1428–1434.
Büchi et al., Helv. Chim. Acta, 1955, vol. 38, pp. 670–679.
Rosenthal, Arch. intern. Pharmacodynamie, 1953, vol. 96, pp. 202–230.

*Primary Examiner*—Alan L. Rotman
*Assistant Examiner*—Natalia Harkaway
*Attorney, Agent, or Firm*—William G. Webb; B. Woodrow Wyatt

[57] ABSTRACT

1-Amino-lower-alkyl-3,4-diphenyl-1H-pyrazoles, useful as anti-depressants and analgesics, are prepared by reduction with an alkali metal aluminum hydride of an ω[1-(3,4-diphenyl-1H-pyrazolyl)]-lower alkanamide; reduction with hydrogen in the presence of ammonia, methylamine, dimethylamine or diethylamine over a catalyst of a 1-(cyano-lower-alkyl)-3,4-diphenyl-1-H-pyrazole; reaction of a 1-(tosyloxy-lower-alkyl)-3,4-diphenyl-1H-pyrazole with a lower-alkylamine; reaction of 3,4-diphenylpyrazole with a halo-lower-alkylamine in the presence of an acid acceptor; or reductive alkylation with formaldehyde of a 1-(3-aminopropyl)-3,4-diphenyl-1H-pyrazole.

7 Claims, No Drawings

1-AMINO-LOWER-ALKYL-3,4-DIPHENYL-1H-PYRAZOLES

RELATED APPLICATIONS

This is a division of my prior, copending application Ser. No. 752,316, filed Dec. 20, 1976, abandoned July 14, 1978.

BACKGROUND OF THE INVENTION (a) Field of the Invention

This invention relates to 1-amino-lower-alkyl-3,4-diphenyl-1H-pyrazoles, useful as anti-depressants and analgesics.

(b) Description of the Prior Art

Rosenthal, Arch. intern. pharmacodynamie, 96, 220–230 (1953) discloses 1-(2-aminoethyl)-3,5-diphenyl-1H-pyrazole having local anesthetic activity; Grandberg et al., Zh. Obsch. Khim. 31, 3700–3705 (1961); C.A. 57, 9839 (1957) disclose 1-(3-aminopropyl)-3,5-diphenyl-1H-pyrazole for which no utility is asserted; Torf et al., Biol. Aktivn. Soedin, Akad. Nauk SSR, 1965, 171–174; C.A. 63, 16329d (1965) disclose 1-(2-diethylaminoethyl)-3,5-diphenyl-1H-pyrazole, for which no utility is described; Jones et al., J. Org. Chem. 19, 1428–1434 (1954) disclose various 1-(2-aminoethyl)-3-phenyl-1H-pyrazoles which were tested and found inactive as gastric secretory stimulants and histaminic agents; and Büchi et al., Helv. Chim. Acta, 38, 670–679 (1955) disclose 1-(2-dimethylaminoethyl)-3-phenyl-4-methyl-1H-pyrazole for which analgesic activity is asserted.

The prior art thus either fails to suggest any utility for the compounds disclosed (Grandberg et al., Torf et al., Jones et al.); and/or it discloses compounds differing from the instant compounds either in the number or positions of the phenyl groups on the pyrazole ring (Rosenthal, Grandberg et al., Torf et al., Jones et al.); or it discloses compounds differing in two or more structural features from the present species (Jones et al., Büchi et al.). In any event, none of the known art suggests the specific group of 1-amino-lower-alkyl-3,4-diphenyl-1H-pyrazoles here disclosed and claimed which owe their desired anti-depressant and analgesic activities to certain precise structural features.

SUMMARY OF THE INVENTION

In a composition of matter aspect, this invention relates to certain 1-[3-(N=B)-propyl]- and 1-[2-(N=B)-ethyl]-3,4-diphenyl-1H-pyrazoles which are useful as anti-depressants and analgesics.

DETAILED DESCRIPTION INCLUSIVE OF THE PREFERRED EMBODIMENTS

More specifically, this invention relates to compounds having the formula:

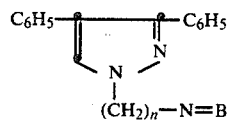

and chemically designated 1-[3-(N=B)-propyl]- and 1-[2-(N=B)-ethyl]-3,4-diphenyl-1H-pyrazoles where n is 2 and N=B is diethylamino; or where n is 3 and N=B is amino, methylamino, dimethylamino or diethylamino. The species where n is 3 and N=B is either dimethylamino or methylamino are particularly useful as antidepressant agents, while those where n is 3 and N=B is amino or diethylamino and those where n is 2 and N=B is diethylamino are useful as analgesic agents.

The compounds of formula I are prepared by reducing, with an alkali metal aluminum hydride, an ω-[1-(3,4-diphenyl-1H-pyrazolyl)]-lower-alkanamide having the formula II:

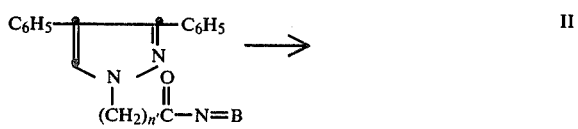

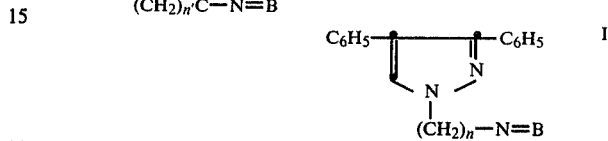

where n and N=B have the meanings given above, and n' is the next lower integer to n. The reaction is preferably carried out in an organic solvent inert under the conditions of the reaction, for example dioxane, diethyl ether or tetrahydrofuran at temperatures from about −10° C. to the boiling point of the solvent used. The method is particularly advantageous for the preparation of compounds where n' is 2 and n is 3. The desired starting materials of formula II are prepared by reaction of 3,4-diphenylpyrazole with a lower-alkyl acrylate in the presence of a strong base, saponification of the resulting ester, conversion of the resulting acid to the corresponding acid chloride, and reaction of the latter with an appropriate amine in the presence of an acid acceptor, e.g. pyridine.

Another method for preparing the compounds of formula I comprises reducing with hydrogen over a Raney nickel catalyst in the presence of ammonia a 1-(cyano-lower-alkyl)-3,4-diphenyl-1H-pyrazole of formula III to produce the corresponding compounds where N=B is amino. If the compounds where N=B is methylamino, dimethylamino or diethylamino are desired, then the reaction is carried out in the presence of methylamine, dimethylamine or diethylamine, respectively. The method is illustrated by the following reaction:

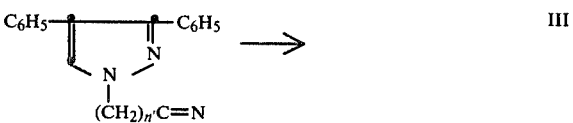

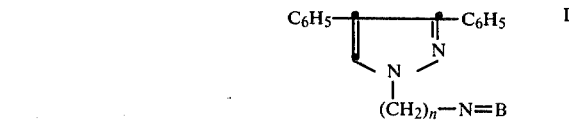

where n and n' have the meanings given above, and N=B is amino, methylamino, dimethylamino or diethylamino. Reduction is carried out in an organic solvent inert under the reaction conditions, for example a lower-alkanol, at ambient temperature and at hydrogen pressures in the range from 50 to about 90 p.s.i. The method is particularly advantageous for the preparation of compounds where n is 3.

The starting materials of formula III where n' is 2 are prepared by reaction of 3,4-diphenylpyrazole with acrylonitrile in the presence of a strong base.

A third method for preparing the compounds of formula I comprises reacting a 1-[3-(tosyloxy)propyl]- or 1-[2-(tosyloxy)ethyl]-3,4-diphenyl-1H-pyrazole having the formula IV with an appropriate amine, H—N=B, as represented by the following reaction:

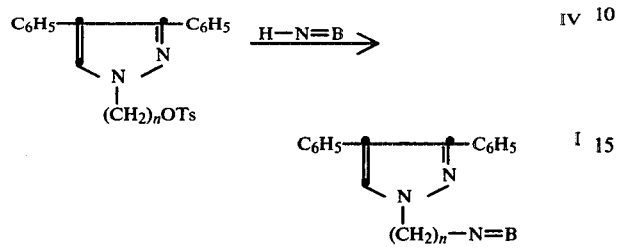

where n and N=B have the meanings given above. The reaction is carried out by heating a mixture of the compound of formula IV with the amine in an organic solvent inert under the conditions of the reaction, for example acetonitrile or a lower-alkanol, at a temperature from about 100 to about 150° C.

The intermediates of formula IV are prepared by condensation of formyldesoxybenzoin [Russell et al., J. Am. Chem. Soc. 76, 5714–5718 (1954)] with an ω-hydroxyalkylhydrazine followed by reaction of the resulting 1-(3-hydroxypropyl)-3,4-diphenyl-1H-pyrazole or 1-(2-hydroxyethyl)-3,4-diphenyl-1H-pyrazole with a toluenesulfonyl halide in the presence of pyridine.

Another method for preparing the compounds of formula I comprises reacting a 3,4-diphenyl-1H-pyrazole with a strong base, for example sodium hydride, in an organic solvent inert under the conditions of the reaction, for example tetrahydrofuran, dioxane or diethyl ether, and reacting the resulting sodium salt with an appropriate halo-lower-alkylamine in the same solvent system at the reflux temperature thereof. The method is illustrated by the following reaction:

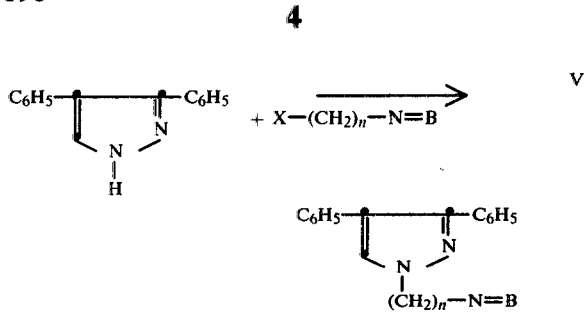

where n and N=B have the meanings given above, and X represents halogen.

Another method for preparing the compounds of formula I where n is 3 and N=B is dimethylamino comprises reducing either with formic acid or with hydrogen in the presence of a catalyst a mixture of 1-(3-aminopropyl)-3,4-diphenyl-1H-pyrazole and at least two equivalents of formaldehyde. The reaction is preferably carried out in an organic solvent inert under the conditions of the reaction, for example a lower-alkanol such as ethanol. A preferred method comprises reducing the reaction mixture with hydrogen over a catalyst at a hydrogen pressure of 50-90 p.s.i., and a preferred catalyst is platinum oxide.

As indicated above, preparation of the final products of formula I requires either the alkylation of 3,4-diphenylpyrazole by Michael addition of a lower-alkyl acrylate or acrylonitrile [here designated Method (a)]; the alkylation of 3,4-diphenylpyrazole with a halo-lower-alkylamine in the presence of an acid-acceptor [here designated Method (b)]; or the introduction of an hydroxy-lower-alkyl group at the 1-position of 3,4-diphenylpyrazole by condensation of formyldesoxybenzoin with an ω-hydroxy-lower-alkylhydrazine [here designated Method (c)]. These various transformations are shown schematically in the following flow diagram:

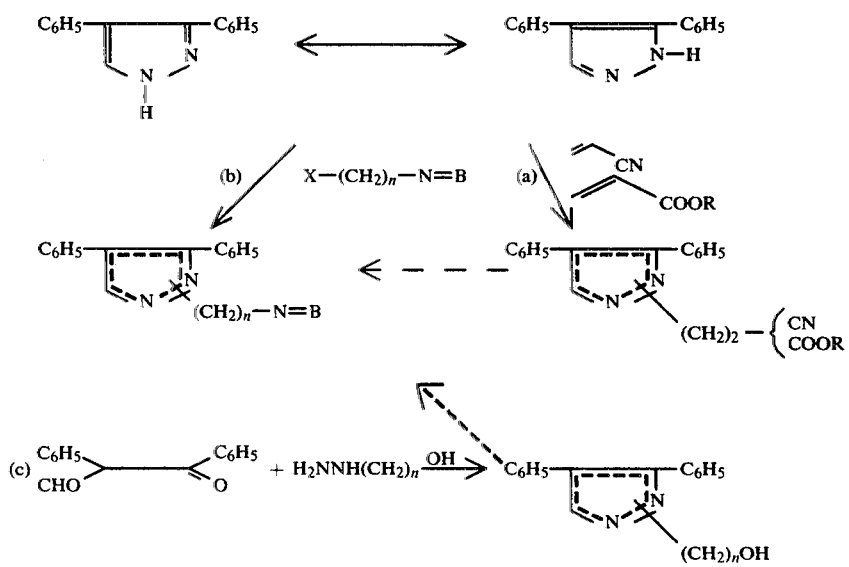

where n, N=B and X have the meanings given above. From the above flow diagram, it will be seen that all three methods result in the formation of a mixture of the 3,4-diphenyl and 4,5-diphenyl products. In Methods (a) and (b), these mixtures result from alkylation of one of the two possible tautomeric forms of the diphenylpyrazole starting material. In Method (c), the mixtures result from the lack of reaction selectivity of the ketone and aldehyde carbonyl groups of the formyldesoxybenzoin starting material. Generally speaking, alkylation with a lower-alkyl acrylate or with acrylonitrile [Method (a)] produces about 85% of the desired 3,4-diphenyl isomer; alkylation with a halo-lower-alkylamine [Method (b)] produces about a 50:50 mixture of isomers; and Method (c) appears to favor formation of the 3,4-isomer. In any event, it is necessary to separate the 3,4- and 4,5-diphenyl isomers from one another at some point in the overall synthesis irrespective of which method is used.

The structural assignments for the 3,4- and 4,5-diphenyl isomers are made on the basis of their ultraviolet and NMR spectra and their behavior on gas chromatography. Thus a consistent and unambiguous relationship can be seen between the isomers in the ultraviolet spectra. One member of each pair of isomers shows absorption maxima at 223 nm and at 249±2 nm, while the other shows absorption maxima at 227±2 and 252±1 nm in 95% ethanol. Moreover the extinction coefficients are generally higher for the 227/252 member of the pair. Thus the ultraviolet spectra can be used to identify an isomer once any particular isomer of the entire series has been assigned a particular structure.

Such an assignment can be made using NMR data. Elguero and Jacquier ]J. Chim. Phys. 63, 1242 (1966)] have shown that in highly polar solvents, such as hexamethyl phosphorotriamide, the proton at the 3-position of a series of 1,4-disubstituted pyrazoles always fell upfield of the 5-position proton. Applying this to the instant series leads to the assignment of the 3,4-diphenyl-substitution to members of the series with the 227/252 uv maxima and of the 4,5-diphenyl-substitution to the 233/249 series, since in the NMR spectra, the same downfield absorption from the 5-position proton is obtained for the 3,4-diphenyl isomer, the upfield absorption from the 3-position being absent. Conversely the same upfield absorption from the 3-position proton is obtained for the 4,5-diphenyl isomer, while the downfield absorption from the 5-position proton is absent.

In the NMR spectra, a completely regular and predictable relationship between members of a pair also obtains for the chemical shifts of the methylene protons adjacent to the nitrogen atom at the 1-position of the pyrazole ring. The 3,4-diphenyl isomer is always found downfield of the 4,5-diphenyl isomer.

Finally the retention times of the isomers on gas chromatography mirror the above-noted dichotomy found in the spectral data, the 3,4-isomer having the longer retention time in all cases.

Due to the presence of a basic amino grouping, the free base form represented by formula I above reacts with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like.

All of the acid-addition salts are useful as sources of the free base forms, by reaction with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic, pharmaceutically-acceptable acids, for example hydrochloric acid, lactic acid, tartaric acid, and the like, are of course employed.

As indicated above, in standard pharmacological test procedures, the compounds of formula I above where n is 3 and N=B is methylamino or dimethylamino and the acid-addition salts thereof have been found useful as anti-depressant agents, while the compounds of formula I above where n is 3 and N=B is amino or diethylamino and those where n is 2 and N=B is diethylamino have been found useful as analgesics.

The compounds of formula I can be administered in the same manner as known anti-depressants and analgesics, i.e. either parenterally or orally in any of the conventional pharmaceutical forms, as for instance solutions, suspensions, tablets, capsules and the like.

The useful properties of the compounds of this invention were demonstrated by standard pharmacological procedures readily carried out by technicians having ordinary skill in pharmacological test procedures, so that the actual determination of the numerical biological data definitive for a particular test compound can be ascertained without the need for any extensive experimentation.

The test procedure used to determine the anti-depressant activity of the compounds of the invention is described as follows: Male Swiss-Webster mice (Taconic Farms) weighing from 19–24 g. were divided into four groups of nine to ten mice per group. The first three groups were administered the test compound at respective doses of 64, 16 and 4 mg./kg. dissolved either in water as a water soluble acid-addition salt or as a suspension in 1% gum tragacanth. The fourth group received the vehicle only. Four hours following medication, all the control and the test animals were medicated with 50 mg./kg. (i.p.) of tetrabenazine and were placed in a photocell activity cage [described by Harris et al., Psychon. Sci., 4, 267 (1966)] equipped with a digital counter to record the number of times that a light beam impinging on a photocell is interrupted during the test period. Beginning thirty minutes after tetrabenazine medication, the photocell units were activated and the photocell counts recorded over a fifty minute period. The compounds were then recorded as being either active or inactive, activity being defined as a significant difference (0.05 level or less, two-tailed) between the drug and control group photocell counts according to the Kruskal-Wallis statistical probability test.

The test procedures used to determine the analgesic activities of the compounds of the invention have been described in detail in the prior art and are as follows: The acetylcholine-induced abdominal constriction test, which is a primary analgesic screening test to measure the ability of a test agent to suppress acetylcholine-induced abdominal constriction in mice described by Collier et al., Brit. J. Pharmacol. Chemotherap. 32, 295 (1968) and the phenyl p-quinone-induced writhing test, also a primary analgesic screening test, designed to measure the ability of a test agent to prevent phenyl p-quinone-induced writhing in mice, described by Pearl and Harris, J. Pharmacol. Exptl. Therap. 154, 319-323 (1966).

The structures of the compounds of this invention were established by the modes of synthesis, by elementary analyses and by ultraviolet, infrared and nuclear magnetic reasonance spectra. The course of reactions and homogeneity of the products were ascertained by thin layer chromatography.

The manner and process of making and using the invention, and the best mode contemplated by the inventor of carrying out the invention will now be described so as to enable any person skilled in the art to which it pertains to make and use the same. The melting points are uncorrected unless noted otherwise.

Preparation of Intermediates

Preparation 1

To a solution of 22 g. (0.1 mole) of 3,4-diphenyl-pyrazole in 150 ml. of dioxane was added 10 ml. of Triton B (benzyl trimethylammonium hydroxide), and the solution then treated dropwise with 26.3 ml. (0.4 mole) of acrylonitrile while maintaining the temperature at 40°-45° C. The mixture was stirred for an additional twenty minutes at ambient temperature, acidified by the addition of 3 ml. of acetic acid and poured into 700 ml. of ice/water. The mixture was then treated with 200 ml. of ethyl acetate and about one tablespoon of sodium chloride, shaken and filtered to remove an insoluble precipitate. The organic layer was separated from the filtrate, and the aqueous layer extracted twice with ethyl acetate. The combined organic extracts were washed with saturated sodium bicarbonate, then with brine, dried over magnesium sulfate, charcoaled, filtered and evaporated to dryness to give a red oil which was crystallized from 60 ml. of methanol. There was thus obtained 13.82 g. of material, m.p. 90°-103° C. which, on gas chromatographic analysis, showed the presence of two isomers in a ratio of 13/87 comprising 13% of the 4,5-diphenyl isomer and 87% of the 3,4-diphenyl isomer of 1-(2-cyanoethyl)-diphenyl-1H-pyrazole.

In another run, a thin suspension of 7.7 g. (0.14 mole) potassium hydroxide and 805 g. (3.65 moles) of 3,4-diphenylpyrazole in 3.4 liters of ethanol was stirred rapidly while treating with 292 ml. (4.4 moles) of acrylonitrile added dropwise over a two hour period. When addition was complete, stirring was continued for two hours while cooling in an external ice bath, and the mixture was then allowed to stand for two days at ambient temperature. The mixture was then cooled once again to 0° C. and the solid product collected and dried to give 723 g. of material, m.p. 103°-108° C. Recrystallization of the latter from ethanol afforded 681 g. of material, m.p. 108°-111° C. (soft. 106° C.) which was shown by vapor phase chromatography to be 92-93% of the 3,4-isomer and 6-7% of the 4,5-diphenyl isomer of 1-(2-cyanoethyl)-diphenyl-1H-pyrazole.

Preparation 2

To a solution of 28 g. (0.127 mole) of 3,4-diphenyl-pyrazole in 130 ml. of dioxane was added 11 ml. of Triton B. The solution was then treated dropwise at ambient temperature with 45 ml. of methyl acrylate over a period of about fifteen minutes. The mixture was stirred for an additional hour and forty-five minutes, acidified to pH 5.5 with acetic acid and then poured onto ice. The mixture was worked up in the manner described above in Preparation 1 to give 40 g. of a mixture of methyl $\beta$-[1-(3,4-diphenyl-1H-pyrazolyl)]-propionate and methyl $\beta$-[1-(4,5-diphenyl-1H-pyrazolyl)]propionate as an oil.

The crude mixture obtained above was dissolved in about 80 ml. of methanol, the solution treated with 130 ml. of a 2 N solution of potassium hydroxide in methanol and then refluxed for two hours. The bulk of the solvent was then removed in vacuo and the residue treated with dilute hydrochloric acid and ethyl acetate. On cooling, the mixture set up into a white mass, which was triturated with water and adjusted to pH 2 with hydrochloric acid. The solid material was collected by filtration to give 40.1 g. of a mixture consisting essentially of about 85% $\beta$-[1-(3,4-diphenyl-1H-pyrazolyl)]-propionic acid and 15% of $\beta$-[1-(4,5-diphenyl-1H-pyrazolyl)]propionic acid. The crude material was slurried with acetonitrile and filtered to give 30.1 g. of the pure 3,4-diphenyl isomer, m.p. 184.5°-187° C.

The latter (7.0 g., 0.024 mole) was slurried in 50 ml. of chloroform and the slurry added to 3.22 g. (0.027 mole) of thionyl chloride. The mixture was refluxed for about an hour with stirring, then charcoaled, filtered and the solvent removed in vacuo from the filtrate. The residue was dissolved in 50 ml. of tetrahydrofuran and the solution added dropwise with stirring to a solution of 25 ml. of 6 N dimethylamine in tetrahydrofuran while maintaining the temperature at about 0°-10° C. When addition was complete the mixture was allowed to warm to ambient temperature, then refluxed for one hour and poured into 150 ml. of ice water and extracted into three 50 ml. portions of ethyl acetate. The combined ethyl acetate extracts were washed with water, then with 10% potassium carbonate, then with brine, dried over sodium sulfate, filtered and taken to dryness to give 6 g. of a pale yellow oil. The latter was chromatographed on 500 g. of silica gel in ethyl acetate with ethyl acetate elution. After removal of about 750 mg. of material, elution was switched to 5% methanol in ethanol to give 3.50 g. of material with $R_f=0.31$ which consisted of $\beta$-[1-(3,4-diphenyl-1H-pyrazolyl)]-N,N-dimethylpropionamide as a yellow gum.

Preparation 3

A solution of 105 g. (0.47 mole) of formyldesoxybenzoin and a molar equivalent amount of 2-hydroxyethylhydrazine in 450 ml. of absolute ethanol was heated under reflux for two and a half to three hours, then cooled, and the solid which precipated was collected by filtration. The filtrate was taken to dryness to give a brown oil which was dissolved in chloroform, washed with water and then evaporated to dryness to give 53 g. of off white material having m.p. 99°–105° C. The latter was recrystallized from a solution of about 40 ml. of ethylene dichloride and 100 ml. of pentane to give 46.5 g. of 1-(2-hydroxethyl)-3,4-diphenyl-1H-pyrazole, m.p. 102°–103° C., shown by gas chromatography to be approximately 97–98% pure 3,4-diphenyl isomer.

A solution of 32.6 g. (0.12 mole) of the latter in 130 ml. of pyridine was mixed with a solution of 24.5 g. (0.13 mole) of p-toluenesulfonyl chloride in 75 ml. of pyridine and the solution stored in a refrigerator for about eighteen hours. The solid which had separated was collected by filtration, and the filtrate poured into about five volumes of ice/water. The mixture was allowed to stand at about 0° C. for two hours, then the liquid decanted from the gummy solid which was slurried with ether to leave a solid material which was slurried with cold methanol to give 15 g. of 1-[2-(4-toluenesulfonyloxy)ethyl]-3,4-diphenyl-1H-pyrazole, m.p. 109°–110° C. as a white solid.

PREPARATION OF THE FINAL PRODUCTS

EXAMPLE 1

A. To a slurry of 13.8 g. (0.05 mole) of 1-(2-cyanoethyl)-3,4-diphenyl-1H-pyrazole described in Preparation 1 above in a solution of 100 ml. of methanol containing anhydrous ammonia was added a small amount of Raney nickel catalyst and the mixture reduced in a Parr shaker at 50 p.s.i. hydrogen pressure. After three days the mixture was filtered, and the filtrate taken to dryness leaving a residue which was dissolved in 40 ml. of isopropanol and 30 ml. of isopropyl acetate. The solution was treated with 20 ml. of 5.7 N hydrogen chloride in ethanol, and the solid which separated was collected, rinsed with additional solvent and dried to give 15.2 g. of 1-(3-aminopropyl)-3,4-diphenyl-1H-pyrazole dihydrochloride, m.p. 177°–188° C. which was shown by gas chromatography to be 94% pure isomer.

B. Following a procedure similar to that described in part A above, 27.3 g. (0.1 mole) of the 87% pure 1-(2-cyanoethyl)-3,4-diphenyl-1H-pyrazole described in Preparation 1 above in a solution of methylamine in ethanol was reduced with hydrogen over a Raney nickel catalyst at 50 p.s.i. and the product, after isolation in the manner described in part A, converted to the hydrochloride salt which was recrystallized from ethanol. There was thus obtained 5.9 g. of 1-[3-(N-methylamino)propyl]-3,4-diphenyl-1H-pyrazole hydrochloride, m.p. 124°–132° C.

C. Following a procedure similar to that described in part A above, in three separate runs, 100 g. (0.36 mole) portions of the 92–93% pure 1-(2-cyanoethyl)-3,4-diphenyl-1H-pyrazole described in Preparation 1 above in a solution containing 110–120 g. of methylamine in 960 ml. of ethanol were reduced over 5 g. of 10% palladium-on-charcoal and the product converted first to the oxalate salt (m.p. 140°–143° C.) which was reconverted to the free base and the latter converted to the dihydrochloride salt which was recrystallized from isopropanol to give a total yield from all three runs of 262 g. of 1-[3-(N,N-dimethylamino)propyl]-3,4-diphenyl-1-H-pyrazole dihydrochloride, m.p. 183°–185° C. (soft. 175° C.). The latter was estimated by thin layer chromatography to contain from 1–2% total impurities. (See Example 2).

EXAMPLE 2

To a stirred slurry of 0.42 g. (0.011 mole) of lithium aluminum hydride in 50 ml. of tetrahydrofuran was added 3.5 g. (0.011 mole) of β-[1-(3,4-diphenyl-1H-pyrazolyl)]-N,N-dimethylpropionamide and the mixture stirred and refluxed for about eighteen hours. The reaction mixture was then decomposed by the careful addition of 0.4 ml. of water followed by 0.6 ml. of ten percent sodium hydroxide, followed by an additional 1 ml. of water. The mixture was stirred for an hour, then filtered, and the filtrate taken to dryness in vacuo. The residue, consisting of 3.0 g. of a yellow oil, was dissolved in isopropyl acetate and the solution treated with 4 ml. of a 6 N solution of hydrogen chloride in ethanol. The solid which separated was collected and recrystallized from isopropanol containing an additional amount of hydrogen chloride in ethanol. There was thus obtained 1.2 g. of 1-[3-(N,N-dimethylamino)propyl]-3,4-diphenyl-1H-pyrazole dihydrochloride, m.p. 170°–174° C.

EXAMPLE 3

A mixture of 29.5 g. (0.073 mole) of 1-[2-(4-toluenesulfonyloxy)ethyl]-3,4-diphenyl-1H-pyrazole and 103 ml. of dimethylamine in 400 ml. of acetonitrile was heated in an autoclave for nine hours at 120°–130° C. The reaction mixture was washed out of the autoclave with acetonitrile, and the mixture was taken to dryness in vacuo. The residue was suspended in 800 ml. of ethyl acetate and the suspension washed with water containing a small amount of sodium hydroxide. The organic layer was then washed with brine, dried and taken to dryness to give 28 g. of a brown oil which was distilled in vacuo. The fraction collected at 81°–100° C./0.01 mm. (15.3 g.) was dissolved in diethyl ether and treated with a solution of hydrogen chloride in methanol. The solid which separated was recrystallized from acetone to give 10.5 g. of 1-[2-(N,N-diethylamino)ethyl]-3,4-diphenyl-1H-pyrazole hydrochloride, m.p. 147°–148° C.

EXAMPLE 4

A mixture of 4.2 g. (0.1 mole) of sodium hydride in 100 ml. of tetrahydrofuran and 22.0 g. (0.1 mole) of 3,4-diphenylpyrazole in 150 ml. of tetrahydrofuran was heated with stirring until a clear solution was obtained. The mixture was then treated with 14.9 g. of N-(3-chloropropyl)-N,N-diethyamine. The solution was refluxed for thirty hours, then filtered and stripped to dryness in vacuo. The residue was taken into ethyl acetate, extracted into dilute hydrochloric acid and the acid solution washed once with ethyl acetate and neutralized with potassium carbonate. The aqueous mixture was then extracted with ethyl acetate and the organic extracts washed twice with brine, dried and taken to dryness to give 20.4 g. of a yellow oil. The latter was dissolved in diethyl ether, treated with a molar equivalent amount of methanolic hydrogen chloride, and the solid which separated after cooling was collected and dried to give 20.2 g. of crude hydrochloride. The latter was reconverted to the free base which was dissolved in chloroform and the chloroform solution washed four times with 125 ml. portions of water. The organic layer was then dried, taken to dryness and the residue redissolved in diethyl ether and treated again with excess methanolic hydrogen chloride. There was thus obtained 16.5 g. of a 1:1 mixture of 1-[3-(N,N-diethylamino)propyl]-3,4-diphenyl-1H-pyrazole hydrochloride and the corresponding isomeric 4,5-diphenyl compound, m.p. 143°–146° C.

The latter (800 mg.) was dissolved in methanol and applied to four 20×40 cm. silica gel thin layer chromatography plates. The plates were eluted with a 19:1 solution of 95% ethanol/concentrated ammonium hydroxide, and the upper one third of the plate, containing material with the higher $R_f$ value, was cut away from the lower two thirds section, and both sections were separately extracted with a 1:1 solution of chloroform/methanol. The higher $R_f$ fraction was shown by gas chromatography to be 97–99% pure 4,5-diphenyl isomer, and the lower $R_f$ fraction was shown to be 82/18 3,4-/4,5-isomer mixture. The higher $R_f$ fraction originally obtained as an oil, was crystallized from actone/hexane to give 75 mg. of 1-[3-(N,N-diethylamino)propyl]-4,5-diphenyl-1H-pyrazole hydrochloride, m.p. 148°–149° C., shown by gas chromatography to be 99.8% pure 4,5-isomer.

The lower $R_f$ fraction, on repeated recrystallization from acetone/hexane, gave 103 mg. of 1-[3-(N,N-diethylamino)propyl]-3,4-diphenyl-1H-pyrazole hydrochloride, m.p. 165°–166° C., shown by gas chromatography to be 98% pure 3,4-isomer. (Note the hydrochloride salts of both isomers were carried through the chromatography and separation despite the use of concentrated ammonium hydroxide in the elution.)

EXAMPLE 5

A solution of 11.5 g. (0.04 mole) of 1-(3-aminopropyl)-3,4-diphenyl-1H-pyrazole and 60 ml. of 35% aqueous formaldehyde in 125 ml. of ethanol was reduced in a Parr shaker over 500 mg. of platinum oxide at 50 p.s.i. hydrogen pressure. Reduction was interrupted after the uptake of 29 p.s.i., another 500 mg. of catalyst was added, and reduction was continued until an additional 39 p.s.i. had been taken up. Reduction was once again interrupted, additional formaldehyde and catalyst were again added and reduction continued until a final 31 p.s.i. had been taken up. The mixture was worked up in the manner described in Example 1A above and the product converted to the hydrochloride salt to give two crops totalling 6.6 g. of 1-[3-(N,N-dimethylamino)propyl]-3,4-diphenyl-1H-pyrazole dihydrochloride, 4.0 g., m.p. 178°–191° C. and 2.6 g., m.p. 185°–191° C.

BIOLOGICAL TEST RESULTS

Results obtained in the anti-tetrabenazine (TB), the acetylcholine (Ach) and the phenylquinone induced writhing tests (PPQ) on the 3,4-diphenyl compounds of the invention are set forth in the table below. All 3,4-diphenyl compounds are identified by the example numbers above where their preparations are described, and all doses are expressed in milligrams per kilogram (mg./kg.).

| Example | TB | Ach | PPQ |
|---|---|---|---|
| 1A | Inac. (a) | $ED_{50} = 11$ (s.c.) | — |
| 1B | Act./16,64 Inac./4 | — | — |
| 2 | Act./4,8,16 Inac./2 | — | — |
| 3 | Inac. (a) | 60%/100 (s.c.) 67%/50 (s.c.) 53%/10 (s.c.) $ED_{50} = 29$ (p.o.) | $ED_{50} = 90$ (p.o.) |
| 4 | Inac. (a) | $ED_{50} = 2.2$ (s.c.) | |

(a) Tested at 4, 16 and 64 mg./kg. (p.o.)

I claim:

1. A member of the group consisting of (A) a 1-[3-(N=B)-propyl]-3,4-diphenyl-1H-pyrazole having the formula:

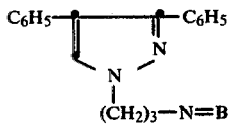

where N=B is methylamino or dimethylamino; and (B) pharmaceutically acceptable acid-addition salts thereof.

2. A member of the group consisting of (A) a 1-[(N=B)-lower-alkyl]-3,4-diphenyl-1H-pyrazole having the formula:

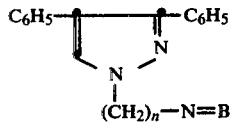

where n is 2 and N=B is diethylamino; or n is 3 and N=B is amino or diethylamino; and (B) pharmaceutically acceptable acid-addition salts thereof.

3. 1-[3-(N,N-Dimethylamino)propyl]-3,4-diphenyl-1H-pyrazole according to claim 1.

4. 1-[3-(N-Methylamino)propyl]-3,4-diphenyl-1H-pyrazole according to claim 1.

5. 1-(3-Aminopropyl)-3,4-diphenyl-1H-pyrazole according to claim 2.

6. 1-[2-(N,N-Diethylamino)ethyl]-3,4-diphenyl-1H-pyrazole according to claim 2.

7. 1-[3-(N,N-Diethylamino)propyl]-3,4-diphenyl-1H-pyrazole according to claim 2.

* * * * *